United States Patent
Lee et al.

(10) Patent No.: US 11,499,148 B2
(45) Date of Patent: Nov. 15, 2022

(54) FATTY MATERIAL FROM WHICH IMMUNITY IS REMOVED AND METHOD FOR MANUFACTURING SAME

(71) Applicant: Hee Young Lee, Seoul (KR)

(72) Inventors: Hee Young Lee, Seoul (KR); Hyun Jin Yang, Seoul (KR)

(73) Assignee: Hee Young Lee, Seoul (KR)

( * ) Notice: Subject to any disclaimer, the term of this patent is extended or adjusted under 35 U.S.C. 154(b) by 1011 days.

(21) Appl. No.: 14/349,796

(22) PCT Filed: Oct. 17, 2012

(86) PCT No.: PCT/KR2012/008474
§ 371 (c)(1),
(2) Date: Apr. 4, 2014

(87) PCT Pub. No.: WO2013/058537
PCT Pub. Date: Apr. 25, 2013

(65) Prior Publication Data
US 2015/0050710 A1    Feb. 19, 2015

(30) Foreign Application Priority Data

Oct. 17, 2011 (KR) .................. 10-2011-0105894

(51) Int. Cl.
| C12N 13/00 | (2006.01) |
| A61L 27/60 | (2006.01) |
| A61L 27/36 | (2006.01) |
| C12N 5/00 | (2006.01) |
| C12N 5/077 | (2010.01) |

(52) U.S. Cl.
CPC ............ *C12N 13/00* (2013.01); *A61L 27/362* (2013.01); *A61L 27/3691* (2013.01); *A61L 27/60* (2013.01); *C12N 5/0081* (2013.01); *C12N 5/0653* (2013.01); *A61L 2430/40* (2013.01); *C12N 2509/00* (2013.01); *C12N 2511/00* (2013.01)

(58) Field of Classification Search
None
See application file for complete search history.

(56) References Cited

U.S. PATENT DOCUMENTS

| | | | | | |
|---|---|---|---|---|---|
| 4,776,173 | A * | 10/1988 | Kamarei | ................ | A61K 35/12 241/23 |
| 5,896,989 | A * | 4/1999 | Ropiak | ................ | A61J 1/1462 206/438 |
| 5,989,498 | A * | 11/1999 | Odland | ................ | A61L 2/0035 422/22 |
| 6,193,891 | B1 * | 2/2001 | Kent | ................ | A61K 35/14 210/502.1 |
| 6,337,113 | B1 * | 1/2002 | Muggli | ................ | B32B 15/08 428/35.2 |
| 6,479,116 | B1 * | 11/2002 | Small, Jr. | ................ | B32B 27/08 428/36.7 |
| 6,908,591 | B2 * | 6/2005 | MacPhee | ................ | A61L 2/0029 422/21 |
| 6,974,796 | B1 * | 12/2005 | Girsh | ................ | A61K 31/726 424/9.1 |
| 7,998,404 | B2 * | 8/2011 | Huang | ................ | A61L 2/081 422/1 |
| 8,084,055 | B2 * | 12/2011 | Voytik-Harbin | ........ | A61L 27/24 424/443 |
| 9,370,536 | B2 * | 6/2016 | Sun | ................ | A61K 35/35 |
| 2003/0099792 | A1 * | 5/2003 | Andersson | ................ | B32B 27/32 428/35.2 |
| 2003/0207137 | A1 * | 11/2003 | Kong | ................ | B32B 27/32 428/515 |
| 2004/0033160 | A1 * | 2/2004 | MacPhee | ................ | A61L 2/0029 422/22 |
| 2004/0126880 | A1 * | 7/2004 | Manders | ................ | A01N 1/0294 435/374 |
| 2004/0191226 | A1 * | 9/2004 | Badylak | ................ | A61K 35/407 424/93.7 |
| 2005/0008626 | A1 * | 1/2005 | Fraser | ................ | A61L 27/3834 424/93.21 |
| 2005/0260176 | A1 * | 11/2005 | Ayares | ................ | A01K 67/0276 424/93.7 |
| 2007/0082059 | A1 * | 4/2007 | Duneas | ................ | A61L 27/46 424/549 |

(Continued)

FOREIGN PATENT DOCUMENTS

| EP | 0819957 | 1/1995 |
| JP | 0616839 U | 3/1994 |

(Continued)

OTHER PUBLICATIONS

Kim et al., Effects of γ-Irradiated Fats on Plasma Lipid Concentrations and Hepatic Cholesterol Metabolism in Rats, Annals of Nutrition and Metabolism, 2001, 45:152-158.*

(Continued)

*Primary Examiner* — Blaine Lankford
(74) *Attorney, Agent, or Firm* — Jeffrey D. Moy; Weiss & Moy (57) ABSTRACT

The present invention relates to a living fatty material from which immunity is removed, and a method for manufacturing the same, and more specifically, to a living fat tissue from which immunity is removed and to a method for manufacturing the same, comprising the steps of collecting fat tissues; irradiating the fat tissues with 20 to 500 kGy of gamma (γ) rays; and applying centrifugal separation of the fat tissues irradiated with gamma rays.

15 Claims, 3 Drawing Sheets

(56) References Cited

U.S. PATENT DOCUMENTS

| | | | |
|---|---|---|---|
| 2011/0091353 A1* | 4/2011 | Burgess | A61L 2/0035 422/22 |
| 2011/0129531 A1* | 6/2011 | Collette | A61K 8/64 424/484 |
| 2011/0151011 A1* | 6/2011 | Flynn | A61L 27/3604 424/490 |
| 2011/0152196 A1* | 6/2011 | Shah | A61L 27/3633 514/17.2 |
| 2012/0181193 A1* | 7/2012 | Wu | B32B 15/08 206/204 |
| 2012/0264190 A1* | 10/2012 | Christman | A61K 9/0019 435/219 |
| 2012/0305426 A1* | 12/2012 | Valaie | A61L 2/26 206/363 |
| 2018/0170017 A1* | 6/2018 | Ettridge | B32B 7/12 |

FOREIGN PATENT DOCUMENTS

| | | |
|---|---|---|
| KR | 1020040041593 | 5/2004 |
| KR | 102007093256 | 9/2007 |
| KR | 100832737 | 5/2008 |
| KR | 1020090055125 | 12/2010 |

OTHER PUBLICATIONS

LifeNet, A Bio-Implants Brief, Allograft Tissue Sterilization Using Allowash XG, Jun. 2007.*

Choi et al., Decellularized extracellular matrix derived from human adipose tissue as a potential scaffold for allograft tissue engineering, J Biomed Mater Res Part A: 97A: 292-299, 2011.*

Kramer, A comparison of procedures to determine free fatty acids in rat heart, Journal of Lipid Research, vol. 19, 1978 (Year: 1978).*

* cited by examiner

Comparative Example 1    Comparative Example 2

FATTY MATERIAL FROM WHICH IMMUNITY IS REMOVED AND METHOD FOR MANUFACTURING SAME

TECHNICAL FIELD

The present invention relates to a living fatty material from which immunity is removed and a method for manufacturing the same. More specifically, the present invention relates to a living fatty material of a person to be transplanted to another person after removing immunities from fatty tissues collected from the person, and a method for manufacturing the same.

BACKGROUND ART

Injection materials for the purpose of volume replacement in human body have been attempted in various ways using numerous materials for the past two centuries. For example, silicone and paraffin which had been used in the past are hardly used at present because they are known to induce immune-related problems such as granuloma. Recently, allogenic dermis or allogenic bones obtained from humans or animals have been processed to be used as transplantation materials. However, they require various additional chemical treatments to remove antigenicity from them by using immune proteins and cells during the engineering process thus requiring much time for obtaining their approval. In addition, even the treatment with the immune proteins and cells cannot guarantee 100% removal of antigenicity because there is still a risk of adverse reactions by the treatment. Furthermore, the engineering process requires an extremely high cost and there is an insufficient supply of cadavers to provide raw materials for transplantation thus making the cost of the consumable materials to be raised as high as about USD 500.00/cc and thus raising a serious economic burden to a person requiring transplantation.

Looking at the recent related technologies both home and abroad, various artificial skin products are under development ranging from an acellular artificial skin to layered cellular living skin equivalent (LSE) obtained by culturing epidermal cells and hypodermal cells of one's own skin and they are close to commercialization. These products are highly expensive because they have undergone a cell-free treatment by using allogenic tissues, or prepared in a biomaterial such as collagen. The cellular LSE can provide an excellent skin wound recovery effect by promptly healing skin wounds and also reducing scars, and autogenic cells or processed allotissues are reportedly have no immune rejection response. In Korea, matrix-type artificial skins using chitosan, collagen, and chitin have been commercialized, and also culture skins where skin cells are cultured on a matrix are under clinical trial but there still remains an issue for its large scale production.

Korean Pat. No. 10-0469661 discloses a method for manufacturing acellular dermal layer for transplantation, which was commercialized into a product, SureDerm, thereby capable of replacing part of biomaterials required for tissue recovery in Korea which had been imported from overseas to Korea. Nevertheless, quite a few biomaterials are still imported as raw materials to Korea for the skin production due to the rather strict rules and regulations on obtaining human skins in Korea. These products, generally known as "filler", are manufactured by using materials such as animal derived materials, artificially synthesized materials, human derived tissues, etc., and they have many disadvantages in terms of convenience in use, consistency, and cost of products.

Other examples of the products include Zyderm®, which was prepared as an injection by using cow collagen; Artecoll®, which is a mixed solution between polymethylmethacrylate beads and collagen; Restylene®, which is a product prepared by using a modified hyaluronic acid; Cymetra®, which is a powder processed product of AltoDerm®, etc. The AlloDerm® (LifeCell, U.S.A.) was prepared by using the skin of a donated dead body by processing the skin into human allogenic acellular dermis and has been commercialize as a transplantation graft or an insert. In the case of the above product, all cells were removed thereby eliminating all the possibilities of immune rejection response, and also had the most advantage in biocompatibility than any known artificial skin products by using the human tissues as they were. In Korea, similar products have been developed but the materials are mostly imported from overseas due to insufficient number of donated dead bodies.

In addition, fat tissues collected from patients with obesity were either discarded or stored for later use. But the stored fat tissues cannot be used after 2 months of storage because neutral lipids such as triacylglycerol and sterol esters inside lipid droplets which are abundant in the fat tissues are spoiled via oxidation or partial oxidation and hydrolysis. Lipid oxidation causes that the reaction product as a result of the oxidation of a highly unsaturated fatty acid to react with an amino compound such as a protein thereby incurring discoloring and loss, and also generating toxic materials such as hydroperoxide or unsaturated aldehyde. Additionally, the fat tissues of animals such as pigs and cows except humans have a lower content of liquid lipid (50-70%) than that of humans, and partially combined with paniculus muscularis. In contrast, human fat tissues are apparently distinguished as allogenic dermis or muscular layer thus having a significantly higher content of liquid lipid than in animals and thus the progress of developing materials for bio transplantation in humans by using human fat tissues has not been noticeable.

About 98% of fat tissues consist of lipid which is in a liquid state, and thus there is difficulty in storing the fat tissues or at the time of transplantation. Furthermore, fat tissues include all the variables in cell culture and thus there have been few attempts for the development of materials from fat tissues to be used for transplantation. Nevertheless, if a microstructure can be retained to some extent while lipids are removed from the fat tissues, and the volume of the fat tissues are partially maintained while sterilization and removal of immunities is possible, the fat tissues will be able to play a role as a material for biotransplantation.

Recently, it has been reported that a greater number of cells are grown and differentiated in a structure like a sponge, and thus it is speculated that the volume of a material is more important than its weight with respect to its in vivo effects or in cell culture. Accordingly, if fat tissues can maintain the microstructure and sterilization and immunities are removed therefrom they will be a more useful material for transplantation than any other biomaterials. Accordingly, there has been a need for the development of a living fatty material for transplantation using fat tissues which enables long term storage, can tolerate a long distance transport, and can be transplanted to another person because immunity is removed therefrom.

DISCLOSURE

Technical Problem

In order to solve the above-described problem of the existing art, the present invention is directed to providing a living fatty material which can be used as a material for transplantation in humans, undergo long term storage, and tolerate a long distance transport. The present invention is also directed to providing a living fatty material with a surface area to which cells can attach thus being suitable as a support for cell culture by removing lipids from the fat tissues.

Technical Solution

In an exemplary embodiment, the present invention provides a method for manufacturing a living fatty material from which immunity is removed, including: collecting fat tissues; irradiating the fat tissues with gamma (γ) ray at a dose of 20-500 kGy; and centrifuging the irradiated fat tissues.

In an exemplary embodiment, the present invention provides a method for manufacturing a living fatty material from which immunity is removed, wherein the gamma ray irradiation is performed at a low temperature of −60° C. to −10° C.

In an exemplary embodiment, the present invention provides a method for manufacturing a living fat material from which immunity is removed, wherein the low temperature is maintained by placing at least one cold energy storage material selected from dry ice, low temperature isopropyl alcohol, ice, and a low temperature metal block within the space for gamma ray irradiation.

In an exemplary embodiment, the present invention provides a method for manufacturing a living fatty material from which immunity is removed, wherein the collecting of fat tissues is performed using a syringe which is treatable with gamma ray irradiation.

In an exemplary embodiment, the present invention provides a method for manufacturing a living fatty material from which immunity is removed, which further includes a packing step after collecting the fat tissues for sealing purpose, wherein the packing is performed by directly using a container where the fat tissues are contained therein, which is treatable with gamma ray irradiation and also includes a connecting cap capable of opening/closing the container.

In an exemplary embodiment, the present invention provides a method for manufacturing a living fatty material from which immunity is removed, wherein the container is made of at least one material treatable with gamma ray irradiation selected from polycarbonate (PC), polypropylene (PP), polyvinylchloride (PVC), polyethylene terephthalate (PET) and glass.

In an exemplary embodiment, the present invention provides a method for manufacturing a living fatty material from which immunity is removed wherein a container for storing the material can be sealed via packing with at least a double layer.

In an exemplary embodiment, the present invention provides a method for manufacturing a living fatty material from which immunity is removed, wherein at least one layer of the packing is made of a material capable of preventing daylight transmittance.

In an exemplary embodiment, the present invention provides a method for manufacturing a living fatty material from which immunity is removed, which further includes a pulverization step before or after the gamma ray irradiation, or before and after the gamma ray irradiation. In an exemplary embodiment, the present invention provides a method for manufacturing a living fatty material from which immunity is removed, wherein the fat tissues are frozen after the collecting, and thawed after the gamma ray irradiation.

In an exemplary embodiment, the present invention provides a method for manufacturing a living fatty material from which immunity is removed, which further includes a lipid removing step after the gamma ray irradiation.

In an exemplary embodiment, the present invention provides a living fatty material from which immunity is removed obtained by gamma ray irradiation at a dose of 20-500 kGy and centrifugation.

In an exemplary embodiment, the present invention provides a living fatty material from which immunity is removed, wherein the gamma ray irradiation is performed at a low temperature of −60° C. to −10° C.

In an exemplary embodiment, the present invention provides a living fatty material from which immunity is removed, wherein the low temperature is maintained by placing at least one cold energy storage material selected from dry ice, low temperature isopropyl alcohol, ice, and a low temperature metal block within the space for gamma ray irradiation.

In an exemplary embodiment, the present invention provides a living fatty material from which immunity is removed, wherein the collecting of the fat tissues is performed by using a syringe container treatable with gamma ray irradiation.

In an exemplary embodiment, the present invention provides a living fatty material from which immunity is removed, wherein, in the packing step after collecting the fat tissues for sealing purpose, the packing is performed by directly using a container where the fat tissues are contained therein, which is treatable with gamma ray irradiation and also includes a connecting cap capable of opening/closing the container.

In an exemplary embodiment, the present invention provides a living fatty material from which immunity is removed, wherein the container is made of at least one material treatable with gamma ray irradiation selected from polycarbonate (PC), polypropylene (PP), polyvinylchloride (PVC), polyethylene terephthalate (PET) and glass.

In an exemplary embodiment, the present invention provides a living fatty material from which immunity is removed, wherein a container for storing the material can be sealed via packing with at least a double layer.

In an exemplary embodiment, the present invention provides a living fatty material from which immunity is removed, wherein, in packing with at least a double layer, at least one layer of the packing is made of a material capable of preventing daylight transmittance.

In an exemplary embodiment, the present invention provides a living fatty material from which immunity is removed, wherein pulverization is additionally performed before or after gamma ray irradiation, or before and after gamma ray irradiation.

In an exemplary embodiment, the present invention provides a living fatty material from which immunity is removed, wherein the fat tissues are frozen after the collecting, and thawed after gamma ray irradiation.

In an exemplary embodiment, the present invention provides a living fatty material from which immunity is removed, wherein a lipid removing step is performed after gamma ray irradiation.

Advantageous Effects

The present invention pertaining to a living fatty material and a method for manufacturing the same allows unnecessary fat tissues collected from mammals to be usable as transplants for humans.

In addition, the living fatty material and the method for manufacturing the same, according to an exemplary embodiment of the present invention, may be usable as a material for transplantation into humans by removing immunity therefrom via gamma ray irradiation.

Furthermore, the living fatty material and the method for manufacturing the same according to an exemplary embodiment of the present invention may be easily treated with gamma ray irradiation by collecting fat tissues using a gamma ray irradiation treatable container or storing the thus collected fat tissues, and as such, they enable long term storage, and can tolerate long distance transport.

Furthermore, the living fatty material and the method for manufacturing the same according to an exemplary embodiment of the present invention may be usable as a material for transplantation because the microstructures such as cell membranes within the fat tissues are maintained as they are.

Furthermore, the living fatty material and the method for manufacturing the same according to an exemplary embodiment of the present invention may be usable as a support for cell culture because the cells can have a surface area sufficient for cell adhesion by removing lipids via pulverization, centrifugation, and the like.

BEST MODE FOR CARRYING OUT INVENTION

Reference will now be made in detail to embodiments, examples of which are illustrated in the accompanying drawings, wherein like reference numerals refer to like elements throughout. In providing explanations regarding the present invention, the detailed explanations on related known arts or constitutions are omitted in order to prevent the misconception on the main aspects of the present description.

Unless specifically stated or obvious from context, as used herein, the term "about" is understood as within a range of normal tolerance in the art with regard to a unique manufacture of a product or a material, and also to prevent the unjustifiable use of the contents of the accurate and exact values disclosed hereinbelow by an unscrupulous infringer.

The present invention relates to a living fatty material from which immunity is removed, which is transplantable to other people after sterilizing the fat tissues collected from humans and removing immunities therefrom.

In an exemplary embodiment of the present invention, a living fatty material from which immunity is removed may be used as a material for transplantation to other people by irradiating collected fat tissues with gamma ray irradiation, thereby removing the intrinsic immunities retained therein and destroying their antigenicity to autogenic cells and biological reactivity.

In an exemplary embodiment of the present invention, fat tissues collected from humans or mammals may be eliminated of bacteria and immunities, and thereby may be used as a material for transplantation. The method for collecting fat tissues may not be particularly limited but may be directly collected by using an injection syringe, etc.

The collected fat tissues may be irradiated with gamma ray irradiation. The gamma ray irradiation is a type of radiations emitted from radioactive materials and an electromagnetic wave.

When fat tissues are irradiated with gamma ray irradiation it may inactivate immunogens present within the fat tissues.

When something other than autogenic cells is transplanted in the body it induces an immune response.

The body is then induced to have antigenicity and biological reactivity against what is being transplanted thereby destroying the same. Therefore, when a tissue of a person is to be transplanted to another person it is essential that the occurrence of an immune response be prevented by removing antigenicity and biological reactivity.

Looking at the causative reasons of immune responses there are areas that induce an immune response in the extra cellular matrix (ECM), and immune responses also occur in cells and DNA, etc. The major component of the ECM is collagen and there are areas on both ends of collagen that induce immune responses. In addition, a lot of immune response materials are contained on the cell surfaces and internal organs.

In the present invention, fat tissues were irradiated with gamma ray irradiation in order to inhibit their immune responses, i.e., to remove the immunities therefrom.

Gamma ray irradiation directly destroys the cells being exposed thereto causing breakdown of DNA thereby leading to death of the cells. In particular, h fatECM, a material present in ECM of a fat tissue, becomes inactivated in the area which induces an immune response when exposed to gamma ray irradiation.

In an exemplary embodiment of the present invention, the nucleic acids (DNA, RNA) contained in the collected fat tissues may be inactivated via gamma ray irradiation at a dose of 20-500 kGy, the immunities in the ECM can be removed, and the fat tissues can be sterilized by effectively destroying bacteria and the like contained therein.

In an exemplary embodiment of the present invention, the gamma ray irradiation may be performed at a dose of 20-500 kGy, preferably at a dose of 40-150 kGy. When the gamma ray irradiation is within the range of 20-500 kGy, the fat tissues can be removed of their immunities without being denatured by inactivating the nucleic acids contained therein, and can also remove bacteria contained therein. In an exemplary embodiment of the present invention, the gamma ray irradiation time may vary depending on the amount of irradiation, for example, when the gamma ray irradiation is at a dose of 80 kGy the irradiation time is about 90-100 hours, and when the gamma ray irradiation is at a dose of 120 kGy the irradiation time is about 110-120 hours. The gamma ray irradiation may be performed at a low temperature, preferably at a temperature from −60° C. to −10° C.

When the gamma ray irradiation is performed at a low temperature cold energy storage material may be used, and the low temperature may be maintained by placing at least one cold energy storage material selected from dry ice, low temperature isopropyl alcohol, ice, and a low temperature metal block within the space for gamma ray irradiation. When dry ice is used as the cold energy storage material it causes the temperature to go down very low and the gamma ray irradiation may be performed at a low temperature of about −60° C. When the gamma ray irradiation is performed at a low temperature it is preferred that the fat tissues be sealed in a container so that they cannot be in direct contact with the cold energy storage material.

In an exemplary embodiment of the present invention, the collecting of the fat tissues may be performed by using a syringe treatable with gamma ray irradiation. When fat tissues can be collected by using a syringe treatable with gamma ray irradiation the collection step becomes more convenient not necessitating the collected fat tissues to be transferred into another container, and also enables to maintain the collected fat tissues in a sealed state. In an exemplary embodiment of the present invention, the collected fat tissues may be packed in a sealed container, wherein the packing may be performed by directly using the container which was used to collect the fat tissues and thus includes the collected fat tissues therein. In addition, the container may be treatable with gamma ray irradiation. In particular, the container may be tightly sealed from the outside, and may include a connecting cap capable of opening/closing the container and is connectable to other containers. The connecting cap may be included at least one, preferably 1 or 2.

In an exemplary embodiment of the present invention, the material to be used for the packable container is preferably one which is treatable with gamma ray irradiation, for example, at least one selected from the group consisting of polycarbonate (PC), polypropylene (PP), polyvinyl chloride (PVC), polyethylene terephthalate (PET), and glass. The material treatable with gamma ray irradiation preferably has a thickness of about from 0.3 mm to 3 mm, and about from 1 mm to 15 mm in the case of glass. Within the above range, the container can be easily treatable with gamma ray irradiation and also the mobility and storage property are also convenient.

In an exemplary embodiment of the present invention, the container may be sealed via packing with at least a double layer, preferably, with a double layer or a triple layer. The reason of packing the container with at least a double layer is to disinfect the external packing of the container at regular intervals of time because the most external packing may be damaged during long distance transport or a long-term storage.

Additionally, when the container is packed with at least a double layer, at least one layer of the packing may be made of a material which can prevent daylight transmittance. By manufacturing the container packing with a material which is not transmittable to daylight, the external packing of the container can be protected from possible damage during long distance transport or long-term storage, or the risk that the fat tissues contained in the container can be prevented from being damaged due to the penetration of daylight thereinto through the container.

In an exemplary embodiment of the present invention, examples of the material which can prevent daylight transmittance may include a metallic material such as aluminum but is not limited thereto.

In an exemplary embodiment of the present invention, living fat tissues may be pulverized, wherein the pulverization may be performed before or after gamma ray irradiation, or before and after gamma ray irradiation.

The pulverization of the fat tissues is performed in order to separate unnecessary materials such as lipids or oils contained from the fat tissues.

Meanwhile, after gamma ray irradiation a step of centrifugation of the fat tissues may be further performed. The centrifugation of the fat tissues is performed in order to separate materials which are unnecessary in fat tissue transplantation. That is, the centrifugation of fat tissues is performed to separate lipids, oils, water, etc., from the extracellular matrix (ECM), which are necessary in fat tissue transplantation. In other words, by performing centrifugation of the fat tissues, ECM present in the fat tissues can be extracted while removing by separation of lipids such as triacyglycerol, sterol ester, oils, water, etc., present in the fat tissues.

The ECM, an extracellular part of multicellular structure, is composed of various three-dimensionally combined structural and functional molecules secreted by cells, and their artificial synthesis is not possible. As the ECM establishes the shapes of structures it plays a crucial role by determining the physical properties such as compressive strength and elasticity, and controlling osmotic pressure and ion penetration of the structures.

In addition, the ECM assists with cell adhesion and cell growth. Accordingly, when the ECM is transplanted to other persons, cells can adhere to ECM and grow therefrom, thus being useful as a material for transplantation.

Meanwhile, the collected fat tissues can be selectively frozen before the gamma ray irradiation. The reason of adding the freezing step is to store the collected fat tissues without decomposition and also to enable long distance transport.

The frozen fat tissues may be thawed after sterilization and removal of immunities therefrom by irradiating with gamma ray.

In an exemplary embodiment of the present invention, the living fatty material may selectively further include a step of removing lipids. Removal of lipids is not performed by centrifugation alone but a lipid removal step may be added before performing the centrifugation.

Lipids may be removed via various methods.

First, lipids may be removed by using a solid material where a microstructure is formed therein so that lipids can be absorbed via osmosis due to surface tension of the lipids. Examples of the solid material may include pulps, filters, sponges, etc., and they absorb lipids by contacting with lipids and remove them thereafter.

Another method of removing lipids may be to use a hydrophilic material which competes with lipids in binding to the surface of a solid material thereby separating lipids. Examples of the hydrophilic material may include water, alcohol, etc., and water or alcohol may be mixed with fat tissues to thereby separate the lipids from other solid materials.

A further method of removing lipids may be to facilitate a relative movement among lipid tissues while they are in contact with each other and increase the opportunities of their mutual contacts to thereby separate and remove the lipids therein. Examples of the methods as such may include oscillation, rotation, rotation on an inclined plane, circulation through a regular range, shaking, etc.

In addition, lipids may be removed by dissolving them in an organic solvent which can dissolve lipids. The thus manufactured living fatty materials may be repacked and stored or transported, and may be used in transplantation to patients.

When the thus obtained living fatty materials are used as a material for transplantation into humans there will not occur any necrosis because their immunities are removed. Furthermore, they can be stored for a long term, and also be used as a material for transplantation because the microstructures contained therein are maintained. In addition, by removing lipids via pulverization and centrifugation there is generated a surface which cells can attach to, and thus they can serve as a support for culturing cells.

Mode for Invention

The following non-limiting Examples serve to illustrate selected embodiments of the invention. It will be appreciated that variations in proportions and alternatives in elements of the components shown will be apparent to those skilled in the art and are within the scope of embodiments of the present invention.

Example 1

Fat tissues were collected from a person using an injection syringe and exposed to gamma ray irradiation. The injection syringe used was treatable with gamma ray irradiation and the injection syringe itself was exposed to gamma ray irradiation. The gamma ray was irradiated at a dose of 120 kGy for about 120 hours. During the gamma ray irradiation, the outside of the injection syringe was contacted with ice for low temperature treatment. Five minutes after the gamma ray irradiation, the fat tissues were centrifuged at 3500 rpm for 5 minutes, and water, oils, and lipids were separated and removed therefrom to thereby obtain a living fatty material. The thus obtained living fatty material was used in animal experiments by injecting them into 9 experimental rats and the results were observed.

Example 2

Fat tissues were collected from a person using an injection syringe and then pulverized. The pulverized fat tissues were put into a packing container treatable with gamma ray irradiation and irradiated with gamma ray. The gamma ray irradiation was performed at a dose of 80 kGy for about 90 hours. During the gamma ray irradiation, the outside of the injection syringe was contacted with ice for low temperature treatment. Five minutes after the gamma ray irradiation, the fat tissues were centrifuged at 3500 rpm for 5 minutes, and water, oils, and lipids were separated and removed therefrom to thereby obtain a living fatty material.

Comparative Example 1

Fat tissues were collected from a person using an injection syringe and then centrifuged at 3500 rpm for 5 minutes without gamma ray irradiation, and water, oils, and lipids were separated and removed therefrom to thereby obtain a living fatty material. The thus obtained living fatty material was used in animal experiments by injecting them into 9 experimental rats and the results were observed.

Comparative Example 2

Fat tissues were collected from a person using an injection syringe and then pulverized. After the pulverization, the fat tissues were centrifuged at 3500 rpm for 5 minutes without gamma ray irradiation, and water, oils, and lipids were separated and removed therefrom to thereby obtain a living fatty material.

The thus obtained living fatty material was used in animal experiments by injecting them into 9 experimental rats and the results were observed.

Figure 1:
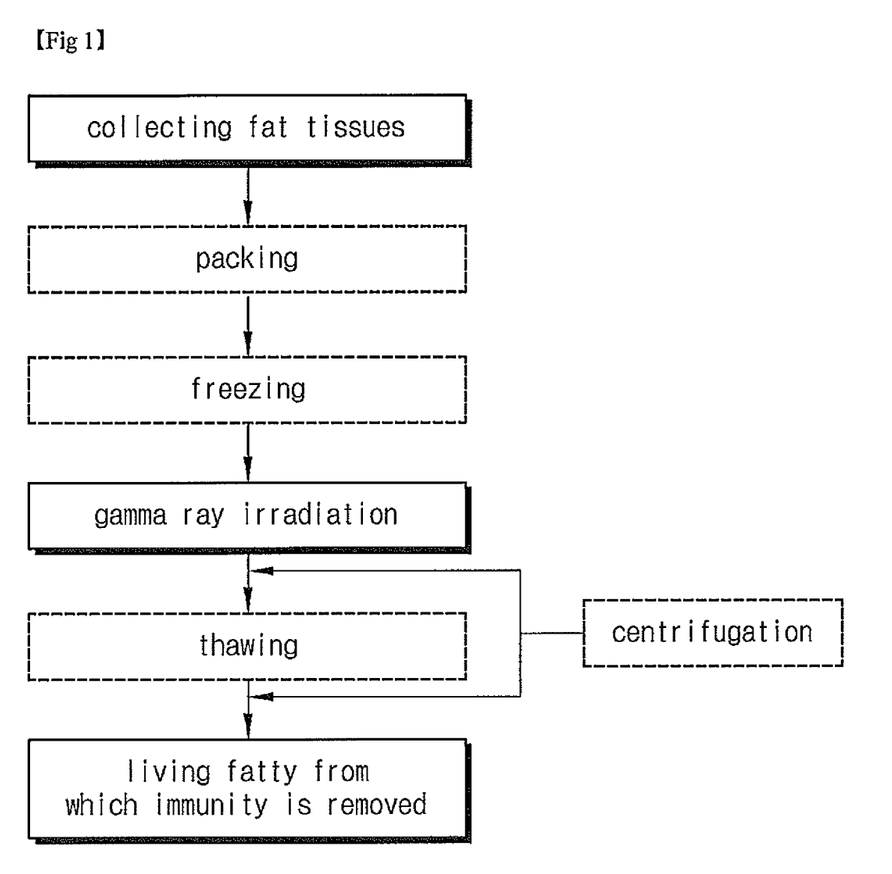
FIG. 1 is a flowchart illustrating a method for manufacturing living fat tissues according to an exemplary embodiment of the present invention.
Figure 2:
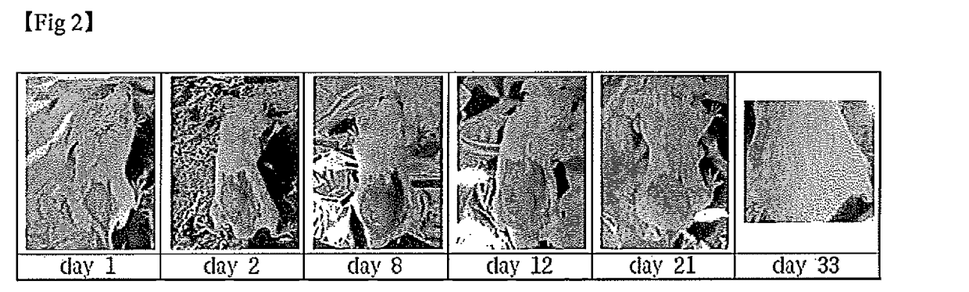
FIG. 2 and FIG. 3 are pictures of the experimental rats taken according to days passed after they were transplanted with the living fatty materials prepared in Example 1 and Example 2 of the present invention.
Figure 3:
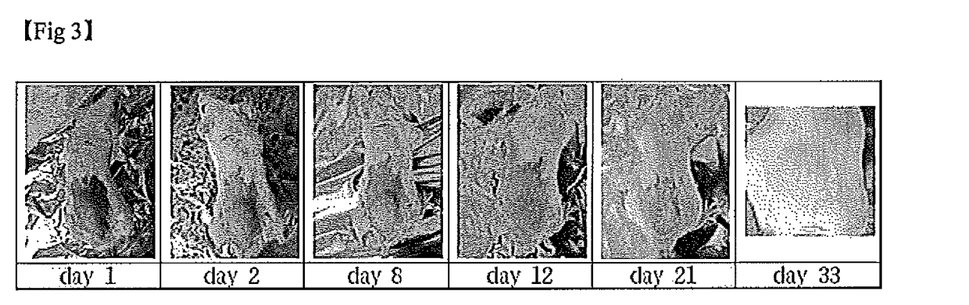
Figure 4:
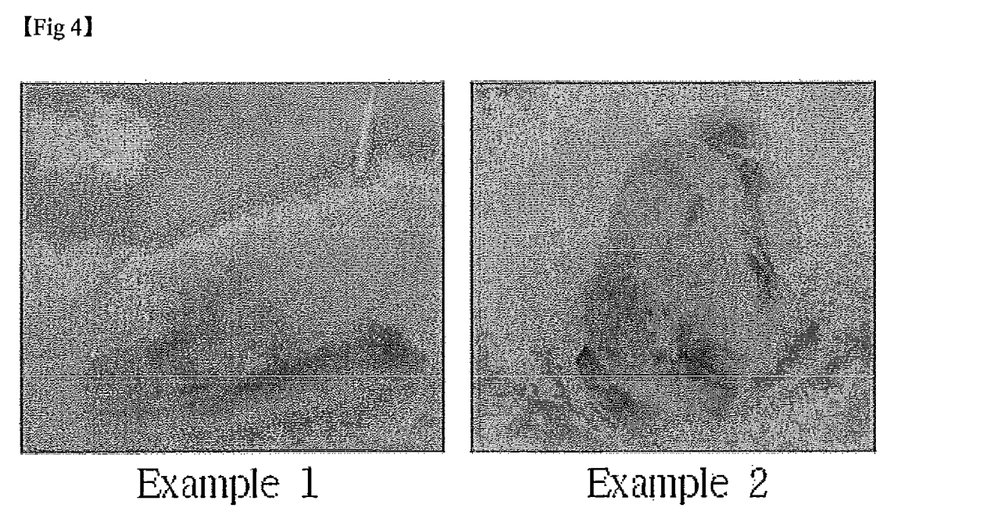
FIG. 4 shows pictures of the cut-out transplanted region of the experimental rats taken four weeks after they were transplanted with the living fatty materials prepared in Example 1 and Example 2 of the present invention.
Figure 5:
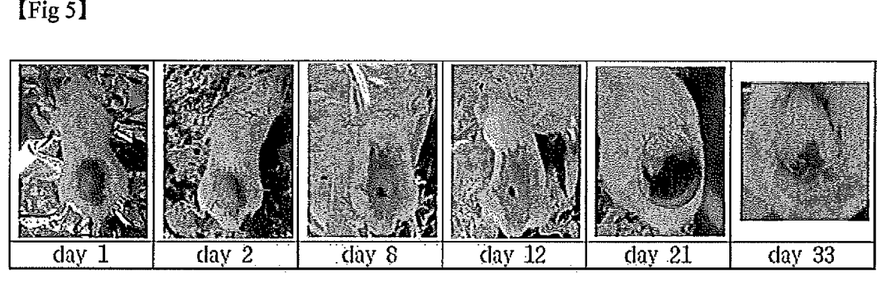
FIG. 5 and FIG. 6 are pictures of the experimental rats taken according to days passed after they were transplanted with the living fatty materials prepared in Comparative Example 1 and Comparative Example 2 of the present invention.
Figure 6:
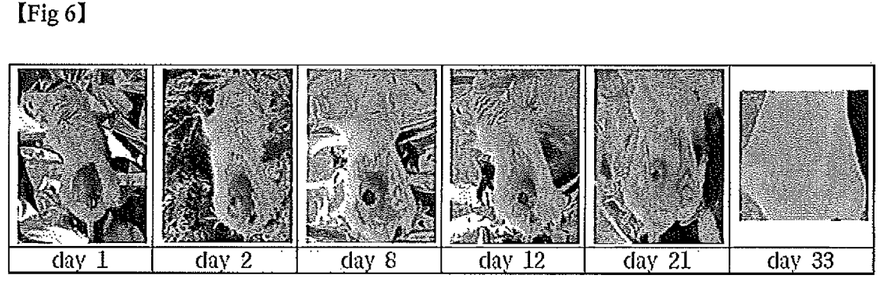
Figure 7:
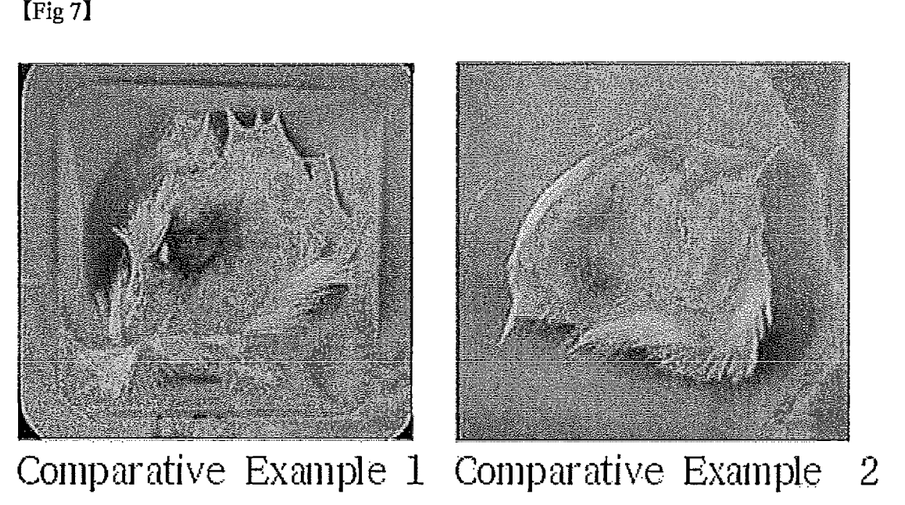
FIG. 7 shows pictures of the cut-out transplanted region of the experimental rats taken four weeks after they were transplanted with the living fatty materials prepared in Comparative Example 1 and Comparative Example 2 of the present invention.

FIG. 2 and FIG. 3 are pictures of the experimental rats taken according to days passed after they were transplanted with the living fatty materials prepared in Example 1 and Example 2 of the present invention. FIG. 4 shows pictures of the cut-out transplanted region of the experimental rats taken four weeks after they were transplanted with the living fatty materials prepared in Example 1 and Example 2 of the present invention. FIG. 5 and FIG. 6 are pictures of the experimental rats taken according to days passed after they were transplanted with the living fatty materials prepared in Comparative Example 1 and Comparative Example 2 of the present invention. FIG. 7 shows pictures of the cut-out transplanted region of the experimental rats taken four weeks after they were transplanted with the living fatty materials prepared in Comparative Example 1 and Comparative Example 2 of the present invention. First, referring to FIG. 5 and FIG. 6, it was observed that the experimental rats on the $8^{th}$ day had necrosis and wounds because the living fatty material injected to the rats was not removed of immunity, and also on the $12^{th}$ day their necrosis became even worse. It was speculated that the above result occurred because the rats damaged the living fatty material, which was not removed of immunity, as non-autogenic cells in the rats' body. Some of the thus damaged cells were shown to recover later (see the 33th day picture in FIG. 6).

Furthermore, although not shown in any of the figures, the living fatty material was also injected to 9 rats, and all of them were observed to have necrosis.

Additionally, referring to FIG. 7, it shows the pictures of the living fatty material observed 4 weeks after it was injected into the rats by cutting it out, and it was observed that the initial shape of the living fatty material was all disappeared. In particular, there was observed necrosis in the skin near the area where the living fatty material was transplanted, and in the inner area of the skin the fat transplanted was decomposed thus losing its initial shape.

On the contrary, it was confirmed that the living fatty material of the present invention was suitable for transplantation.

Referring to FIG. 2 and FIG. 3, the living fatty material was removed of its immunity, and thus when it was injected to experimental rats it was not reacting as an antigen in the rats thus not causing necrosis but settling down by taking a certain amount of volume in the transplanted rats.

That is, there was no necrosis or wounds in the transplanted rats and it was confirmed that the external shape of the rats was maintained as the living fatty material was injected.

Referring to FIG. 4, it shows the pictures of the living fatty material observed 4 weeks after it was injected into the rats by cutting it out, and it was observed that the initial shape of the living fatty material at the time of injection was almost maintained to show at least 90% of the initial shape.

From the foregoing, it was confirmed that the living fatty material of the present invention was removed of its immunity, and its initial shape at the time of injection was maintained without any noticeable change thus being suitable as a material for transplantation.

While exemplary embodiments of the present invention have been described in detail, the protection scope of the present invention is not limited to the foregoing embodiments and it will be appreciated by those skilled in the art that various substitutions, modifications and changes using the basic concept of the present invention defined in the appended claims are also included in the protection scope of the present invention.

The invention claimed is:

1. A method for manufacturing an extracellular matrix (ECM) which is deimmunized and decellularized, comprising:
    collecting fat tissues in a syringe, the syringe treated by gamma radiation prior to collecting the fat tissue in the syringe;
    freezing the fat tissue collected and stored in the syringe;
    irradiating the frozen fat tissues collected and stored in the syringe with gamma radiation at a dose of 40-150 kGy at a temperature from −60° C. to −10° C. for a period of 90 to 120 hours to reduce the immunogenic capacity of the fat tissues by inactivating the nucleic acids contained therein;
    thawing of the irradiated frozen fat tissue;
    absorbing lipids from the irradiated fat tissue after thawing via osmosis with an absorbent solid material, the absorbent solid material forming a microstructure retaining a volume size of the irradiated fat tissue;
    centrifuging the irradiated fat tissues; and
    extracting the extracellular matrix (ECM).

2. The method for manufacturing the extracellular matrix (ECM) which is deimmunized and decellularized, according to claim 1, wherein the low temperature is maintained by placing at least one cold energy storage material selected from the group consisting of: dry ice, low temperature isopropyl alcohol, ice, and a low temperature metal block within the space for gamma ray irradiation, wherein the fat tissue is separated from and does not touch the cold energy storage material.

3. The method for manufacturing the extracellular matrix (ECM) which is deimmunized and decellularized, according to claim 1, packing the syringe in a sealed container is treatable with gamma ray irradiation.

4. The method for manufacturing the extracellular matrix (ECM) which is deimmunized and decellularized, according to claim 3, the sealed container has a cap for opening and for sealing the sealed container.

5. The method for manufacturing the extracellular matrix (ECM) which is deimmunized and decellularized, according to claim 4, wherein the sealed container is made of at least one material treatable with gamma ray irradiation selected from polycarbonate (PC), polypropylene (PP), polyvinylchloride (PVC), polyethylene terephthalate (PET) and glass.

6. The method for manufacturing the extracellular matrix (ECM) which is deimmunized and decellularized, according to claim 4, wherein the sealed container is sealed with at least a double layer packing material, wherein one layer is to disinfect external surfaces of the sealed container.

7. The method for manufacturing the extracellular matrix (ECM) which is deimmunized and decellularized, according to claim 6, wherein at least one layer does not transmit light.

8. The method for manufacturing the extracellular matrix (ECM) which is deimmunized and decellularized, according to claim 1, wherein the fat tissues are pulverized before and after the gamma ray irradiation.

9. The method for manufacturing the extracellular matrix (ECM) which is deimmunized and decellularized, according to claim 1, wherein irradiating the fat tissues comprises irradiating the fat tissue with gamma radiation at a dose of 80 kGy for a period of 90 to 100 hours.

10. The method for manufacturing the extracellular matrix (ECM) which is deimmunized and decellularized, according to claim 1, wherein irradiating the fat tissues comprises irradiating the fat tissue with gamma radiation at a dose of 120 kGy for a period of 110 to 120 hours.

11. The method for manufacturing the extracellular matrix (ECM) which is deimmunized and decellularized, according to claim 4, wherein the container is sealed with a triple layer packing material.

12. The method for manufacturing the extracellular matrix (ECM) which is deimmunized and decellularized, according to claim 5, wherein the sealed container has a thickness of 0.3 mm to 3 mm if formed from polycarbonate (PC), polypropylene (PP), polyvinylchloride (PVC), or polyethylene terephthalate (PET).

13. The method for manufacturing the extracellular matrix (ECM) which is deimmunized and decellularized, according to claim 5, wherein the sealed container has a thickness of 1 mm to 15 mm if formed of glass.

14. The method for manufacturing the extracellular matrix (ECM) which is deimmunized and decellularized, according to claim 1, wherein the absorbent solid material is a sponge retaining the volume size of the irradiated fat tissue.

15. A method for manufacturing an extracellular matrix (ECM) which is deimmunized and decellularized, comprising:
    collecting fat tissues in a container treatable by gamma radiation prior to collecting the fat tissue in the container;
    freezing the fat tissue collected and stored in the container;
    irradiating the frozen fat tissues collected and stored in the container with gamma radiation at a dose of 40-150 kGy at a temperature from −60° C. to −10° C. for a period of 90 to 120 hours to reduce the immunogenic capacity of the fat tissues by inactivating the nucleic acids contained therein;
    thawing of the irradiated frozen fat tissue;
    pulverizing the irradiated fat tissue to separate lipids and oils from the fat tissue;
    absorbing lipids from the irradiated fat tissue after thawing via osmosis with an absorbent solid material, the absorbent solid material forming a microstructure retaining a volume size of the irradiated fat tissue;
    centrifuging the irradiated fat tissues; and
    extracting the extracellular matrix (ECM).

* * * * *